United States Patent [19]

Maan

[11] 4,143,486

[45] Mar. 13, 1979

[54] HYBRID WHEAT

[75] Inventor: Shivcharan S. Maan, Fargo, N. Dak.

[73] Assignee: Research Corporation, New York, N.Y.

[21] Appl. No.: 833,444

[22] Filed: Sep. 15, 1977

[51] Int. Cl.$^2$ .............................................. A01H 1/02
[52] U.S. Cl. ..................................... 47/58; 47/DIG. 1
[58] Field of Search .............................. 47/58, DIG. 1

[56] References Cited

U.S. PATENT DOCUMENTS

| | | | |
|---|---|---|---|
| 2,753,663 | 7/1956 | Jones | 47/58 |
| 2,994,599 | 8/1961 | McRae | 47/DIG. 1 |
| 3,710,511 | 1/1973 | Patterson | 47/58 |
| 4,051,629 | 10/1977 | Galinat | 47/58 |

OTHER PUBLICATIONS

Hybrids of Wheat, Rye, Aegilops and Haynaldia, Sando, Journ. of Hered., vol. 26, 1935, pp. 229–232.
A Proposal for Hybrid Wheat—Franckowiak et al., Crop Science, Sep.–Oct. 1976, pp. 725–727.

Primary Examiner—Robert E. Bagwill
Attorney, Agent, or Firm—Clyde F. Willian; S. Z. Szczepanski

[57] ABSTRACT

Seeds of alloplasmic wheat, which contain at least one specific nuclear gene (Ms) and a cytoplasm which interacts with the specific nuclear gene (Ms) or genes (Ms Ms) to maintain the plant fertile, are treated by a mutagenic agent and, if necessary selfed to obtain seeds having embryos that contain only mutated nuclear genes (ms ms). The seeds having embryos without at least one specific nuclear gene (Ms), produce plants which are male sterile (A-line). The A-line plants are pollinated with pollen from euplasmic or alloplasmic wheat (R-line), having chromosomes including specific nuclear genes (Ms Ms), to produce hybrid wheat seeds. The available A-line seeds may be multiplied by crossing the A-line plants with B-line plants to produce A-line seeds. The B-line seeds are produced by pollinating A-line plants with pollen from plants (D-line) which contain cytoplasm that maintains fertility of the plants irrespective of presence or absence of specific nuclear gene (Ms) and which contain specific nuclear genes (Ms Ms). The pollen from plants grown from the resulting seeds is used to pollinate D-line plants. The resulting seeds are planted and the plants are self pollinated producing seeds which have embryos containing Ms Ms, Ms ms, or ms ms genes and cytoplasm that maintains fertility of the plants regardless of the presence of specific nuclear gene (Ms) or genes (Ms Ms). The seeds having embryos with ms ms genes are selected as the B-line seeds.

25 Claims, 3 Drawing Figures

HYBRID WHEAT

BACKGROUND OF THE INVENTION

This invention relates to breeding of crop plants. In particular, it relates to producing hybrid wheat seeds on a commercial scale.

Controlled cross pollination of plants has been utilized by plant breeders for production of hybrid strains of plants which combine desirable qualities of the original parents. The desired first generation hybrid plants produced by controlled cross pollination have uniform qualities, including the size, height and genetic composition of plant products of economic importance. Since the progenies of the first generation hybrid plants have uneven physical characteristics and differ widely in genetic composition, in order to retain the advantages of a uniform, high quality hybrid crop, the farmer must be supplied with hybrid seeds each time he plants his crop.

One approach for controlling cross pollination of plants is to use cytoplasmic male sterility. In onion, for example, cytoplasmic male sterility can be introduced into one inbred line by backcrossing a fertile line which possesses some desired characteristics into plants that have cytoplasmic male sterility. The inbred male-sterile line is then planted in alternate strips with a male fertile inbred line, in an isolated field. The cross pollination produces, on the male sterile plants, hybrid onion seeds for a commercial crop.

The cytoplasmic male sterility was also utilized in production of hybrid corn seeds as described in the U.S. Pat. No. 2,753,663. Unlike in onion where the vegetative plant parts are of economic value, in corn it is the seed that is harvested. Since male sterile corn plants produce no seeds, a hybrid produced in accordance with a method for production of onion hybrids would be useless to the farmer. The problem was solved by utilizing a fertility restoring plant for the final cross resulting in a hybrid corn seed.

The researchers have attempted to apply the method disclosed in U.S. Pat. No. 2,753,663 to wheat; however, despite continuing efforts, commercially satisfactory restorer plants have not been found. The development of a satisfactory hybrid wheat system has been complicated by the fact that the wheat flower is bisexual and since in wheat the anthers are in the florets, the plants are practically always self pollinated. The location of the wheat anthers inside the florets and the fact that pollen is shed before flowers open makes introduction of male sterility in wheat by physical means (such as manual emasculation) commercially unfeasible. A genetic system, based on cytoplasmic sterility, appears to be the only feasible way for commercial production of hybrid wheat seeds.

The invention satisfies the long felt need for a relatively simple, commercially feasible method of producing hybrid wheat seeds.

Thus one object of the invention is to provide a genetic method for a production of hybrid wheat seeds.

Another object of the invention is to provide a commercially feasible and reliable method for production of hybrid wheat seeds.

A further object of the invention is to use cytoplasmic genetic sterility to produce hybrid wheat seeds having desirable properties.

Still another object of the invention is to provide a genetic method for producing hybrid wheat seeds, which does not require special development of the restorer line and in which conventional common wheat cultivars can be used as the restorer line.

Other objects of the invention will become apparent to those skilled in the art upon studying this disclosure.

SUMMARY OF THE INVENTION

Figure 1:
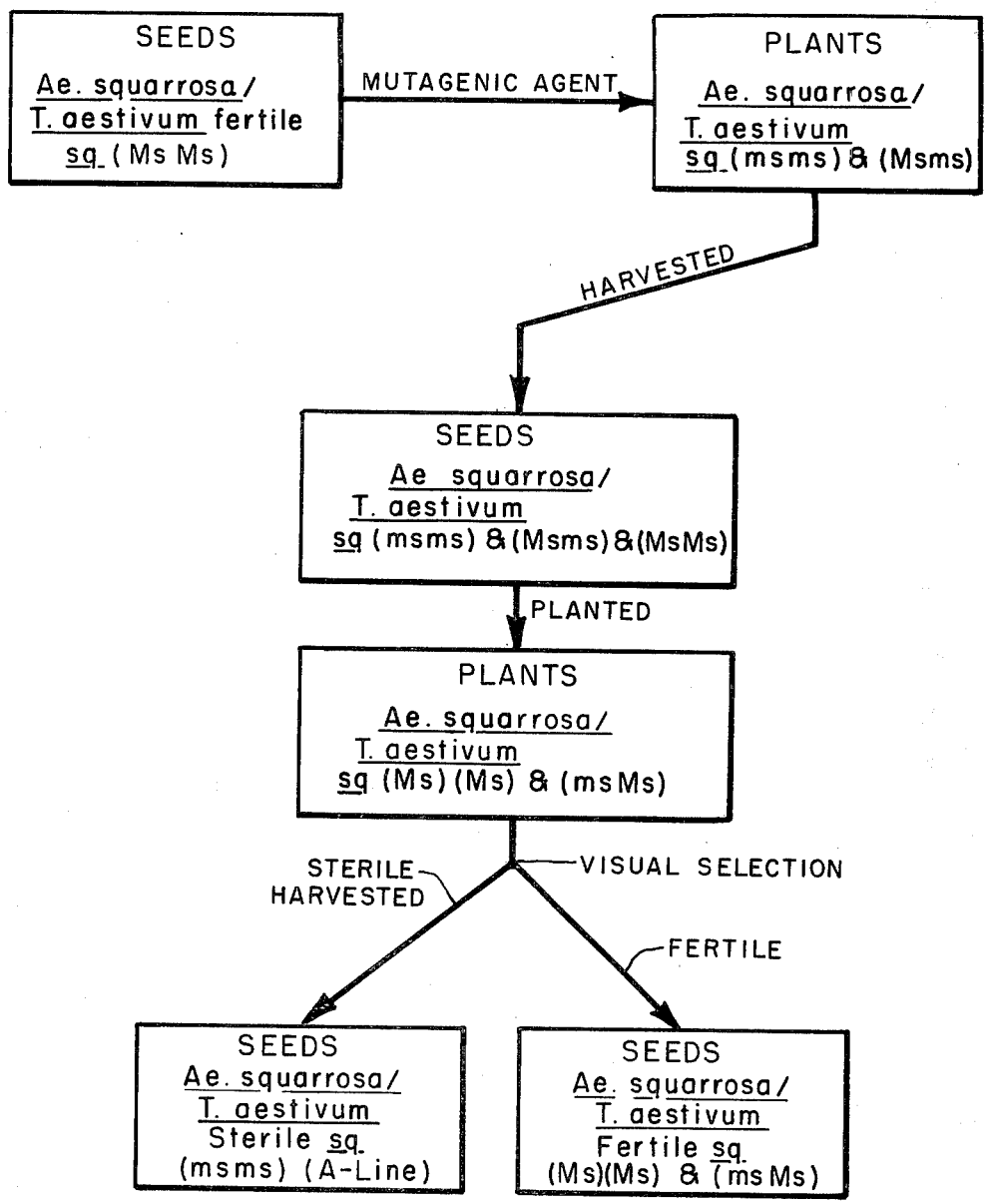
FIG. 1 depicts a sequence of steps for the production of cytoplasmically male-sterile plants (A-line) to be used for the production of hybrid wheat in accordance with one embodiment of the method of this invention.

In accordance with one aspect of the invention, fertile alloplasmic wheat plants, in which fertility is maintained by at least one specific nuclear gene (Ms) interacting with the cytoplasm, are treated to induce mutations of the specific nuclear gene (Ms) or genes (Ms Ms). Those plants, in which all specific nuclear genes (Ms Ms) are changed by the treatment to mutated nuclear genes (ms ms) and which are therefore male sterile, are selected as A-line seeds. The embryos of seeds, which after treatment contain one mutated nuclear gene (ms) and one specific nuclear gene (Ms), are selfed and those of the resulting seeds that contain only mutated nuclear (ms ms) genes are selected as A-line seeds. The A-line seeds are planted and cross pollinated with a compatible wheat plant (R-line) having specific nuclear genes (Ms Ms) required for maintaining of fertility in the cytoplasm of A-line plants. The resulting hybrid wheat seeds have the cytoplasm of the A-line plants and at least one fertility maintaining specific nuclear gene (Ms).

In accordance with another aspect of the invention, the maintainer plants (B-line) are developed as follows. The A-line plants are cross pollinated with compatible wheat plants (D-line) having cytoplasm, which maintains the plant fertile regardless of the presence or absence of the specific nuclear gene (Ms) or genes (Ms Ms), and having chromosomes which have homozygous specific nuclear genes (Ms Ms). The pollen of the plants grown from the seeds produced by the cross pollination is used to pollinate D-line plants. The seeds produced on the D-line plants are grown and the plants are self pollinated. Some of the resulting seeds from each plant are planted and tested to determine which of the seeds have embryos containing only the mutated nuclear genes (ms ms). The seeds of the plants that are determined to have the mutated nuclear genes (ms ms) and no specific nuclear gene (Ms) or genes (Ms Ms) are selected as B-line seeds.

In accordance with a further aspect of the invention, there is provided a method for a commercial production of hybrid wheat seeds. The seeds of alloplasmic wheat, having cytoplasm that interacts with at least one specific nuclear gene (Ms) to maintain the fertility of the plant, are treated by a mutagenic agent to induce mutations of the specific nuclear genes (Ms Ms) into mutated nuclear genes (ms ms). The seeds, having embryos containing only mutated nuclear genes (ms ms) (i.e. no specific nuclear genes (Ms Ms)), are selected as A-line seeds, either directly or by selfing the plants containing one mutated nuclear gene (ms) and one specific nuclear gene (Ms) and selecting those resulting seeds that contain only mutated nuclear genes (ms ms). The A-line seeds are grown and the plants are pollinated by pollen from compatible wheat plants (D-line) having cytoplasm which remains fertile irrespective of the presence of specific nuclear gene (Ms) or genes (Ms Ms) and having chromosomes which include specific nuclear genes (Ms Ms) that are capable of maintaining fertility of the A-line cytoplasm. The resultant seeds are planted and the pollen therefrom is used to pollinate the D-line plants. The seeds produced on D-line plants are then grown and self pollinated (selfed). The seeds of the self pollinated plants, that contain only the mutated nuclear genes (ms ms) are then selected as B-line seeds. The B-line seeds are planted. The pollen from the B-line plants is used to pollinate A-line plants. The A-line plants pollinated by pollen from B-line plants produce seeds containing embryos which have genetic composition of A-line plants. Thus, the A-line seeds are quickly multiplied. The A-line seeds are grown and the plants are crossed with compatible wheat plants (R-line), that have chromosomes containing at least one specific nuclear gene (Ms), which maintains fertility of A-line cytoplasm, producing hybrid wheat seeds.

Other aspects of the invention will become apparent to those skilled in the art upon studying this specification and the appended claims.

DETAILED DESCRIPTION OF THE INVENTION

The seeds of fertile alloplasmic wheat, in which fertility is maintained as the result of the interaction between at least one specific nuclear gene (Ms) and the cytoplasm, are treated to induce mutations of the specific nuclear genes (Ms Ms). As the result of the treatment, the specific nuclear genes (Ms Ms) become mutated nuclear genes (ms ms) which do not maintain fertility of the plants having the cytoplasm present in the alloplasmic wheat plant. Most seeds, in which mutation occurs, contain after treatment in their embryos one specific nuclear gene (Ms) and one mutated nuclear gene (ms). All seeds are planted and the plants are selfed. The resulting seeds include those that possess only mutated nuclear genes (ms ms) in their embryos. The seeds of those plants or their progeny that have only mutated nuclear genes (ms ms) and therefore exhibit cytoplasmic male sterility, are selected as A-line plants. The A-line plants are cross pollinated by pollen from compatible wheat plants (R-line) which have chromosomes that contain specific nuclear genes (Ms Ms) needed for maintaining the fertility in the A-line plants. The cross produces hybrid wheat seeds which have the cytoplasm of the A-line plants and have chromosomes that include at least one specific nuclear gene (Ms) necessary for maintaining the fertility of the hybrid plant.

In practice, only a small number of plants grown from the treated seeds exhibit cytoplasmic sterility (A-line). An additional phase, of extreme importance to the commercial production of hybrid wheat seeds, may be added to the method of this invention to produce maintainer plants (B-line) which when cross pollinated with the A-line plants produce seeds which have genetic composition of A-line plants. Since each A-line plant, when pollinated by the pollen of a B-line plant, produces a large number (250–500) of A-line seeds, the development and use of the B-line permits a rapid multiplication of the available A-line seeds. The A-line plants grown from seeds produced by pollen of B-line plants are used for the final cross to obtain hybrid wheat seeds.

The B-line is developed in accordance with this invention as follows. The A-line plants are cross pollinated with pollen of compatible wheat plants (D-line) having chromosomes which include specific nuclear genes (Ms Ms) which are capable of making plants having the A-line cytoplasm fertile and having cytoplasm that maintains fertility of the plants, regardless of the presence or absence of the specific genes (Ms Ms). The seeds, resulting from the cross, are planted and the pollen grown from these plants is used to cross pollinate D-line plants. The seeds obtained from the cross have fertile cytoplasm of D-line plants and contain either chromosomes having only fertility maintaining genes (Ms Ms) or having a specific nuclear gene (Ms) dominating a mutated gene (ms). The plants grown from these seeds are self pollinated. The seeds produced by self pollination have one of the following three types of embryos:

1. having only specific nuclear genes (Ms Ms);
2. having both a specific nuclear gene (Ms) and a mutated nuclear gene (ms); and
3. having only mutated nuclear genes (ms ms).

All three types of seeds contain D-line cytoplasm; therefore, all plants grown from these seeds are fertile. The B-line seeds are those that contain only mutated nuclear genes (ms ms). To determine which of the seeds are the B-line seeds, the seeds are planted and the pollen from each grown plant is used to pollinate a separate A-line plant. A record of which plant pollen is supplied to which A-line plant, is kept. The resulting seeds are harvested and planted. The plants are visually inspected to determine whether they are fertile or sterile. The seeds of plants, which supplied pollen that produced all sterile progeny when crossed with A-line plants, are selected as B-line seeds.

The B-line plants are then grown from the B-line seeds and crossed with A-line plants. The resulting seeds have a genetic composition of A-line plants. The step of crossing B-line plants with A-line plants can be repeated as often as needed to obtain the desired number of A-line seeds. The seeds of A-line plants are then planted and crossed with R-line plants to produce hybrid wheat seeds.

Throughout this disclosure, the term "alloplasmic wheat" shall mean wheat that has nucleus of wheat and an alien cytoplasm, i.e., cytoplasm which is different from that of common wheat. The term "euplasmic wheat" shall mean wheat plant having wheat cytoplasm and wheat nucleus. The term "compatible wheat plants" shall mean wheat plants that can be cross pollinated to produce seeds.

Two types of seeds are required to initiate the production of hybrid wheat seeds in accordance with this invention:

1. seeds that upon treatment with mutagenic agent become A-line seeds (predecessor of A-line) and,
2. R-line seeds.

The predecessor of A-line seeds are alloplasmic wheat seeds having a cytoplasm that interacts with at least one specific nuclear gene (Ms) to make the plant fertile. The R-line seeds are wheat seeds which contain the specific nuclear genes (Ms Ms) and which are genetically compatible with the A-line plants.

If the method includes multiplication of A-line seeds, D-line seeds are also required. The D-line seeds have cytoplasm that remains fertile regardless of the presence or absence of the specific nuclear genes (Ms Ms) and have chromosomes that include the specific nuclear genes (Ms Ms) and no mutated genes (ms ms). It should be noted that D-line plants can also serve as R-line plants.

Alloplasmic wheat seeds, that are preferred as A-line predecessor, have Aegilops cytoplasm and *Triticum aestivum* nucleus. Especially preferred are the seeds of alloplasmic wheat plants having cytoplasm of the following Aegilops species: *Ae. squarrosa, Ae. cylindrica, Ae. ventricosa, Ae. crassa, Ae. juvenalis,* and *Ae. uniaristata*.

The preferred R-line seeds include euplasmic and alloplasmic *T. aestivum*. Especially preferred are the following plants: euplasmic *T. aestivum* and alloplasmic *T. aestivum* having cytoplasm and specific nuclear genes of *T. timopheevi, T. zhukovskyi, T. araraticum*.

Those skilled in the art can ascertain, with a minimum amount of experimentation, whether a given plant is suitable for the use in the given system for production of hybrid wheat seeds in accordance with the method of this invention and whether given wheat plants are compatible.

The treatment of predecessor A-line seeds can be accomplished by any method which produces point mutations on the chromosomes. For example, the seeds can be treated with mutagenic chemical substances, such as, diethyl sulphate, ethylene imine, ethyl methanesulfonate, and nitroso ethyl urea, or with ionizing radiation from sources, such as, X-rays, gamma rays and Co 60. The radiation having fequency from about $10^{17}$ cycles/sec to about $10^{19}$ cycles/sec and intensity from about 10 rad/min to about 10,000 rad/min is preferred. The duration of the treatment varies depending on the specific type of the treatment but the duration should be long enough to induce point mutations on the chromosomes but should be terminated before inducing non-viability in seeds or seedlings treated. The preferred treatment with ethyl methanesulfonate lasts from about 12 to about 24 hours. The usual duration of the irradiation in the preferred range of frequency and intensity is from about 1 to about 50 hours.

The preferred method of producing hybrid wheat seeds can be subdivided into the following two phases:
1. production of the A-line;
2. production of the hybrid wheat seeds.

The following additional two phases are needed if multiplication of A-line seeds is employed to produce commercial quantities of hybrid wheat seeds.
3. production of the B-line;
4. multiplication of the A-line.

It is contemplated that in a commercial application, the A line and B line plants are produced first. Then the A-line seeds are multiplied and finally hybrid wheat seeds are produced by crossing A-line plants with the R-line plants. The preferred embodiment of the invention will now be described in reference to the drawings; the sequence of steps will be that of a commercial application.

Production of A-line

The seeds of alloplasmic *T. aestivum* having specific nuclear genes (Ms Ms), which maintain fertility of its *Ae. squarrosa* cytoplasm are soaked in a water solution of the mixture of an alkali metal salt of a strong acid and an alkali metal hydroxide, such as, potassium acid phosphate and sodium hydroxide, for a period of time sufficient to allow the solution to fully permeate the seeds. The relative amounts of the alkali metal salt and of the alkali metal hydroxide are such as to maintain the water solution of pH between 6 and 10 and preferably between 7.5 and 8.5. The concentration of alkali metal salt and of alkali metal hydroxide can vary considerably. The preferred range of concentration of alkali metal salt is from about 0.01M (M=molar) to about 0.1M and the preferred concentration of alkali metal hydroxide is from about 0.001M to about 0.05M. The specially preferred ranges of concentration of alkali metal salt and alkali metal hydroxide are from about 0.03M to about 0.07M and from about 0.005M to about 0.015M, respectively. The temperature of the presoaking can vary considerably, the preferred range being from about 50° F. (10° C.) to about 80° F. (27° C.).

The soaked seeds are contacted with a mutagen, such as, water solution of ethyl methane sulfonate (EMS) for a sufficient period of time at such conditions including concentration, pH and temperature as to induce point mutations in the chromosomes in the seeds. The usual ranges for the treatment are as follows: EMS concentration, in a buffer solution of the same composition as for presoaking, from about 0.05M to about 0.3M, pH range from about 6 to about 10, temperature from about 50° F. (10° C.) to about 80° F. (27° C.).

Some of the treated seeds become inviable or they produce sterile plants as the result of non-genetic effect (toxic) on seeds and seedlings. Such non-genetic sterility is generally not inheritable. Furthermore, statistically in most of the embryos of seeds that undergo mutation, only one specific nuclear gene is mutated. To assure that only those plants that contain only mutated nuclear genes (ms ms) are chosen as male-sterile A-line plants, the treated seeds are grown. All the seeds grown have embryos containing, *Ae. squarrosa* cytoplasm and *T. aestivum* nucleus (as shown in FIG. 1). The seeds have one of the three combinations of genes: ms ms, Ms Ms, Ms ms. Statistically ms ms combination is unlikely to occur in the first generation of plants grown from the treated seeds, therefore, the assumption is made that all plants fall into the last two categories. As depicted in FIG. 1, all the seeds are planted and grown. The resulting plants are self pollinated (selfed) to produce seeds that include those having only mutated nuclear genes (ms ms). The seeds are harvested and planted in rows. Each row contains seeds from one plant. Some of the seeds from each plant are saved. To determine whether the plants are sterile or fertile, all plants are visually inspected at anthesis. The sterile plants have malformed anthers and their florets remain open longer than those of the fertile plants. Those rows that contain a large proportion of sterile plants come from seeds that have only mutated genes (ms ms). The remaining seeds from plants that produced sterile seeds are selected as A-line seeds. This is because, since the specific nuclear gene (Ms) is dominant with respect to mutated nuclear gene (ms), only plants having homozygous recessive nuclear genes (ms ms) exhibit genetic sterility. The remaining seeds of those plants are saved as additional source of A-line seeds.

Production of B-line

Figure 2:
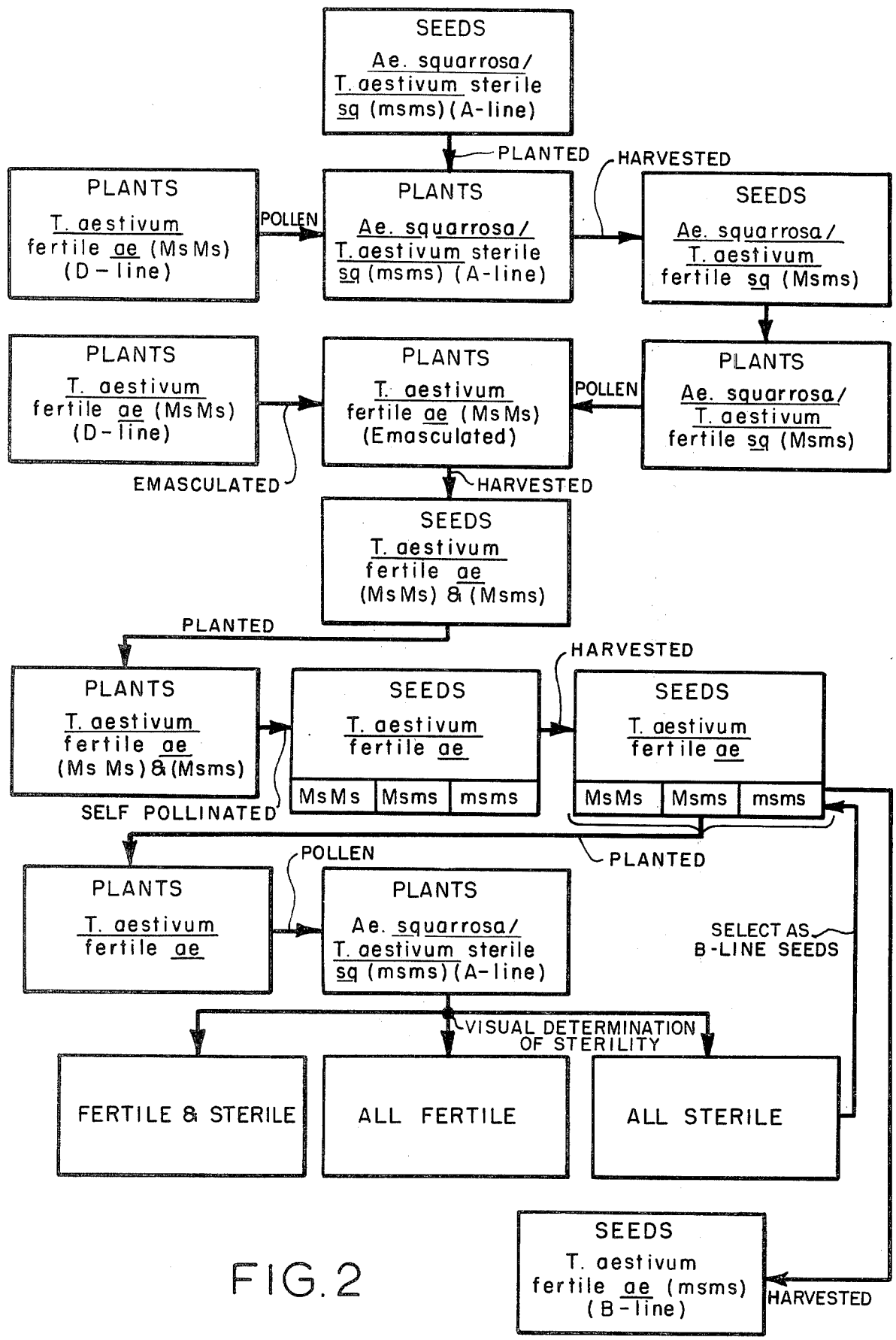
FIG. 2 depicts a sequence of steps for production of B-line plants which are used to multiply the available male sterile seeds (A-line) in accordance with one embodiment of this invention.

Referring now to FIG. 2, the A-line seeds are planted and the plants grown are crossed with *T. aestivum* plants (common wheat). The chromosomes of *T. aes-*

*tivum* contain specific nuclear genes (Ms Ms) which can maintain or restore fertility of plants having *Ae. squarrosa* cytoplasm. The plants having *T. aestivum* cytoplasm remain fertile regardless of the presence or absence of the specific nuclear genes (Ms Ms). The seeds produced by the cross have *Ae. squarrosa* cytoplasm and *T. aestivum* chromosomes containing both a specific fertility maintaining or restoring gene (Ms) and a mutated nuclear gene (ms). Since the mutated nuclear gene (ms) is recessive, it is dominated by the fertility maintaining or restoring gene (Ms) and the plants grown from these seeds are male fertile. The male fertile plants are then crossed with *T. aestivum* (common wheat) plant, but this time the *T. aestivum* plant being the female parent. To prevent self pollination and to make the desired cross, the florets of the *T. aestivum* plants are manually emasculated, as by removing anthers with tweezers. All of the resulting plants from the cross have *T. aestivum* cytoplasm and chromosomes that either contain all specific nuclear gene (Ms) (homozygous) or one specific nuclear gene (Ms) gene and one mutated nuclear gene (ms) (heterozygous). The seeds of these plants are grown and the plants are selfed. The embryos of the resulting seeds have *T. aestivum* cytoplasm and any of the three combinations of genes: Ms ms, Ms Ms and ms ms. Since plants containing *T. aestivum* cytoplasm remain fertile irrespective of presence of specific nuclear gene (Ms), all seeds produce fertile plants.

To select the seeds that have embryos containing homozygous mutated nuclear genes (ms ms), the following procedure is followed. Some of the seeds from each plant are planted and grown. The pollen from each plant is used to pollinate a separate A-line plant or a separate spike on an A-line plant. A record of which A-line plant is pollinated by pollen from which plant, is kept. The resulting seeds are harvested and planted. The resulting plants are visually examined to determine whether they are sterile or fertile in accordance with the procedure discussed before (i.e. by examining their anthers and checking the time period during which florets remain open). The seeds of those plants, which produced functional pollen but which resulted in all male sterile progeny when crossed with male sterile A-line plants, are selected as B-line seeds.

Multiplication of the A-line

Figure 3:
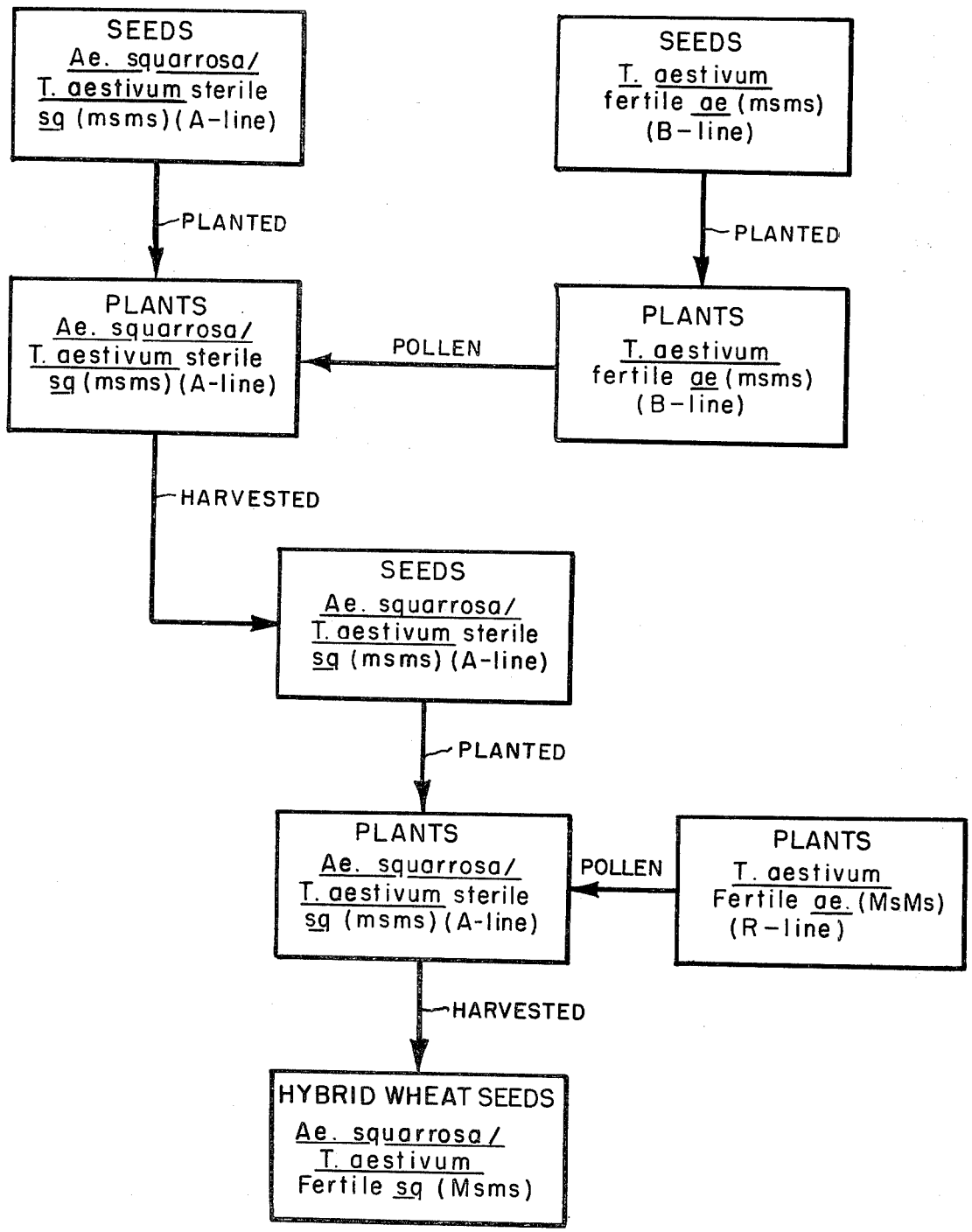
FIG. 3 depicts a sequence of steps for multiplying available A-line seeds and for producing hybrid wheat seeds in accordance with one embodiment of the present invention.

Referring now to FIG. 3, the B-line seeds are planted and these plants are crossed with the A-line plants. The B-line plants i.e., plants that have *T. aestivum* cytoplasm and chromosomes that include the mutated recessive genes (ms ms) and no specific nuclear gene (Ms) produce seeds in A-line plants which have a genetic composition of A-line plants. Since each A-line plant generally produces from about 250 to about 500 seeds, the number of available A-line seeds is quickly multiplied.

Production of Hybrid Wheat Seeds

As illustrated in FIG. 3, the A-line seeds are then planted and cross pollinated with the pollen from *T. aestivum* (euplasmic) plants (common wheat). The euplasmic *T. aestivum* plants (R-line) have *T. aestivum* cytoplasm and *T. aestivum* nucleus which contains specific nuclear genes (Ms Ms) which are capable of maintaining or restoring fertility of plants having *Ae. squarrosa* cytoplasm. The resulting hybrid wheat seeds have *Ae. squarrosa* cytoplasm and *T. aestivum* nucleus which includes one specific nuclear gene (Ms) and one mutated nuclear gene (ms). Since the Ms gene is dominant over the ms gene, the plants grown from the hybrid wheat seeds are fertile.

The following example is intended to further illustrate the invention. It is not intended to restrict the scope of the claimed invention in any manner.

EXAMPLE

Two Phase Production of Hybrid Wheat Seeds

Five hundred seeds from plants having *Ae. squarrosa* cytoplasm and *T. aestivum* nucleus, were presoaked for 8 hours at a temperature of 21° C. in a water solution of potassium acid phosphate and sodium hydroxide adjusted to pH 8. The seeds were removed from the buffer solution and immersed in a solution comprising 0.35 volume percent of ethyl methanesulphate (EMS) and the rest buffer solution having the same composition as the presoaking solution. The EMS-buffer solution was adjusted to pH 8 and maintained at 21° C. during the treatment.

After 16 hours, the seeds were removed from the EMS-buffer solution and planted in a greenhouse. The spikes of the resultant plants were bagged and the plants were allowed to self pollinate. The 45,000 seeds obtained from self pollination were harvested and planted in the field. The seeds were planted about 3 to 4 inches apart within the rows, and space between the rows was about 2.5 to 3.0 feet. The plants were visually examined for anther abnormalities at the time when florets started opening, i.e., after 3 to 5 days after spike emergence from the topmost leaf sheet on the primary tiller of a plant. One or more spikes of plants having abnormal anthers were bagged to exclude the possibility of seed set resulting from cross pollination from the neighboring fertile plants. Those plants that had malformed anthers and had florets that remained opened, were considered completely or highly sterile. Completely or highly sterile plants were crossed with *T. aestivum* cultivars Chris. The resulting seeds from the crossed spikes from 39 of the 45,000 plants were harvested for evaluation as follows. The seeds from crosses of the 39 plants were planted in the greenhouse. The spikes of the plants were bagged to obtain selfed seeds. The selfed seeds were planted and grown in the field. The plants were visually examined for sterility in accordance with the technique described above. The seeds from plants that produced sterile plants were chosen as A-line seeds. The A-line seeds were planted in alternate rows with the seeds of *T. aestivum* cultivar Chris and the resulting plants were allowed to cross pollinate resulting in hybrid wheat seeds, which produced fertile plants when grown.

Many changes and modifications will occur to those skilled in the art upon studying this disclosure. All changes that are within the spirit of the invention are intended to be included within its scope as defined by the appended claims.

I claim:

1. A method for producing hybrid wheat seeds which comprises:
   (a) inducing mutation of a specific nuclear gene in embryos of seeds of alloplasmic wheat plants, having chromosomes of wheat and a cytoplasm which is maintained fertile as the result of interaction between it and at least one specific nuclear gene;
   (b) selfing plants grown from seeds of step "a" to produce seeds;

(c) selecting from seeds produced in step "b" those that contain only mutated nuclear genes in their embryos and are therefore male sterile; and, (d) crossing plants grown from the seeds of step "c" with compatible wheat plants, having chromosomes containing specific nuclear genes capable of maintaining fertility of the cytoplasm of plants produced in step "c", to produce hybrid wheat seeds having cytoplasm of the alloplasmic wheat plant and embryo having at least one fertility maintaining specific nuclear gene dominating the mutated nuclear gene.

2. A method as claimed in claim 1 wherein the seeds of alloplasmic wheat have Aegilops cytoplasm and *Triticum aestivum* nucleus.

3. A product produced in accordance with the method of claim 2.

4. A method as claimed in claim 1 wherein the seeds of alloplasmic wheat are selected from the group consisting of *Ae. squarrosa/T. aestivum, Ae. cylindrica/T. aestivum, Ae. ventriosa/T. aestivum, Ae. crassa/T. aestivum, Ae. juvenalis/T. aestivum,* and *Ae. uniaristata/T. aestivum,* and the compatible wheat plant is selected from the group consisting of *T. aestivum, T. aestivum/T. timopheevi, T. aestivum/T. zhukovskyi,* and *T. aestivum/T. araraticum*.

5. A product produced in accordance with the method of claim 4.

6. A method as claimed in claim 1 wherein the seeds of step "a" are *Ae. squarrosa/T. aestivum* and the compatible wheat plant is *T. aestivum*.

7. A method as claimed in claim 6 wherein the mutations are induced by treatment with a mutagenic chemical.

8. A product produced in accordance with the method of claim 7.

9. A method as claimed in claim 6 wherein the mutations are induced by ionizing radiation.

10. A method as claimed in claim 6 wherein the step of inducing mutation comprises:

soaking the seeds in a water solution of a mixture of an alkali metal salt of a strong acid and an alkali metal hydroxide for a sufficient period of time to allow water solution to fully permeate the seeds; and contacting the seeds removed from the water solution of the soaking step with ethyl methansulfonate for a sufficient period of time and at such conditions including temperature, pH and concentration as to induce said mutation, the contacting being terminated before said seeds become nonviable.

11. A method as claimed in claim 1 wherein the mutations are induced by treatment with a mutagenic chemical.

12. A method as claimed in claim 1 wherein the mutations are induced by ionizing radiation.

13. A product produced in accordance with the method of claim 1.

14. A method for producing seeds to be used for multiplying alloplasmic wheat A-line seeds having chromosomes of wheat containing only mutated specific genes and cytoplasm maintaining fertility of a plant only in the presence of at least one specific nuclear gene, said method comprising the following steps:

(a) crossing the plants grown from said A-line seeds with compatible wheat plants having specific nuclear genes capable of maintaining fertility of the cytoplasm of the alloplasmic A-line wheat plant and cytoplasm that remains fertile regardless of the presence of a least one said specific nuclear gene;

(b) pollinating said compatible wheat plants with pollen from plants grown from seeds of step "a";

(c) selfing plants grown from seeds obtained in step "b" to obtain seeds including B-line seeds containing in their embryos fertile cytoplasm of the compatible wheat plants and only mutated specific genes, said B-line seeds when grown into plants and crossed with said A-line plants producing seeds having genetic composition of A-line plants;

(d) selecting B-line seeds from seeds of step "c".

15. A method as claimed in claim 14 wherein A-line plants are *Ae. squarrosa/T. aestivum* and the compatible wheat plant is *T. aestivum*.

16. A product produced in accordance with the method of claim 14.

17. A method for producing male-sterile alloplasmic wheat seed which comprises the following steps:

(a) inducing mutation of a specific nuclear gene in embryos of seeds of alloplasmic wheat plants, having chromosomes of wheat and a cytoplasm which is maintained fertile as the result of interaction between it and at least one specific nuclear gene;

(b) selfing plants grown from seeds of step "a" to produce seeds; and, (c) selecting from seeds produced in step "b" those that contain only mutated nuclear genes in their embryos and are therefore male sterile.

18. A method as claimed in claim 17 wherein the seeds of alloplasmic wheat are selected from the group consisting of *Ae. squarrosa/T. aestivum, Ae. cylindrica/T. aestivum, Ae. ventriosa/T. aestivum, Ae. crassa/T. aestivum, Ae. juvenalis/T. aestivum,* and *Ae. uniaristata/T. aestivum,* and the compatible wheat plant is selected from the group consisting of *T. aestivum, T. aestivum/T. timopheevi, T. aestivum/T. zhukovskyi,* and *T. aestivum/T. araraticum*.

19. A method of claim 18 wherein said first compatible wheat plants are the same as said second compatible wheat plants.

20. A method as claimed in claim 19 wherein the seeds of alloplasmic wheat are selected from the group consisting of *Ae. squarrosa/T. aestivum, Ae. cylindrica/T. aestivum, Ae. ventriosa/T. aestivum, Ae. crassa/T. aestivum, Ae. juvenalis/T. aestivum,* and *Ae. uniaristata/T. aestivum,* and the compatible wheat plant is selected from the group consisting of *T. aestivum, T. aestivum/T. timopheevi, T. aestivum/T. zhukovskyi,* and *T. aestivum/T. araraticum*.

21. A product produced in accordance with the method of claim 17.

22. A method for producing hybrid wheat seeds which comprises the following steps:

(a) inducing mutations of fertility maintaining nuclear genes into mutated nuclear genes in seeds of an alloplasmic wheat plant, having cytoplasm depending for its fertility on the interaction with at least one fertility maintaining nuclear genes;

(b) selfing plants grown from said seeds to obtain seeds;

(c) selecting seeds producing male fertile plants, said seeds having in their embryos only mutated nuclear genes;

(d) crossing the plants grown from seeds of step "c" with a first compatible wheat plant having a cytoplasm remaining fertile regardless of the presence of said specific nuclear genes and having chromosomes containing said specific nuclear genes;
(e) pollinating said first compatible wheat plant with the pollen from the plants grown from seeds of step "d";
(f) selfing plants grown from the seeds produced in step "e";
(g) selecting from seeds produced in step "f" those that contain only mutated nuclear genes;
(h) crossing plants grown from seeds selected in step "g" with plants grown from seeds of step "c";
(i) crossing plants grown from seeds produced in step "h" with a second compatible wheat plant having chromosomes containing said specific nuclear genes to produce seeds of a hybrid wheat plant.

23. A product produced in accordance with the method of claim 22.

24. A method for producing hybrid wheat seeds which comprises the following steps:
(a) treating seeds of *T. aestivum*, having homozygous specific nuclear genes interacting with its alien *Ae. squarrosa* cytoplasm to maintain fertility, to cause mutation of specific nuclear gene into mutated nuclear gene, said *Ae. squarrosa* cytoplasm requiring interaction with at least one specific nuclear gene to maintain fertility;
(b) selfing plants grown from the treated seeds and selecting those resultant seeds containing homozygous mutated nuclear genes;
(c) crossing male sterile plants from seeds of step "b" with T. aestivum plants to produce seeds;
(d) pollinating T. aestivum plants with pollen of plants grown from seeds produced in step "c",
(e) selfing plants grown from seeds produced in step "d";
(f) selecting seeds from step "e" having homozygous mutated nuclear genes;
(g) crossing plants grown from seeds selected in step "f" with plants grown from seeds selected in step "b" to multiply the seed having *Ae. squarrosa* cytoplasm and homozygous mutated nuclear genes in its *T. aestivum* nucleus;
(h) crossing plants having *Ae. squarrosa* cytoplasm and homozygous mutated nuclear genes in *T. aestivum* nucleus with euplasmic *T. aestivum* to produce hybrid wheat seeds.

25. A product produced in accordance with the method of claim 24.

* * * * *